United States Patent
Urrutia

[19]
[11] Patent Number: 6,106,504
[45] Date of Patent: Aug. 22, 2000

[54] DRIP CHAMBER FOR MEDICAL FLUID DELIVERY SYSTEM

[76] Inventor: Hector Urrutia, 1801 S. 5th St., Suite 102, McAllen, Tex. 78593

[21] Appl. No.: 09/115,640

[22] Filed: Jul. 15, 1998

[51] Int. Cl.⁷ .................................................. A61M 5/00
[52] U.S. Cl. .......................................... 604/251; 604/122
[58] Field of Search ................... 604/7, 27, 30, 604/122, 123, 246, 251–255, 322, 325, 403, 406, 407; 128/760, 763, 765, 766

[56] References Cited

U.S. PATENT DOCUMENTS

| | | |
|---|---|---|
| 2,762,532 | 9/1956 | Packwood, Jr. . |
| 3,126,125 | 3/1964 | Eggers . |
| 3,490,655 | 1/1970 | Ledgett . |
| 3,664,339 | 5/1972 | Santomieri . |
| 3,854,637 | 12/1974 | Muller, Jr. et al. . |
| 3,921,630 | 11/1975 | McPhee . |
| 3,970,490 | 7/1976 | Raines et al. . |
| 4,138,020 | 2/1979 | Steiner et al. . |
| 4,227,525 | 10/1980 | Lundquist . |
| 4,317,473 | 3/1982 | Gaydos . |
| 4,395,260 | 7/1983 | Todd et al. . |
| 4,548,600 | 10/1985 | Ruschke . |
| 4,583,979 | 4/1986 | Palti . |
| 4,601,414 | 7/1986 | Lawson . |
| 4,601,712 | 7/1986 | Cole et al. . |
| 4,615,694 | 10/1986 | Raines . |
| 4,998,926 | 3/1991 | Alchas . |
| 5,489,385 | 2/1996 | Raabe et al. . |
| 5,575,779 | 11/1996 | Barry . |

*Primary Examiner*—Wynn Wood Coggins
*Assistant Examiner*—Deborah Blyveis
*Attorney, Agent, or Firm*—Oliff & Berridge, PLC

[57] ABSTRACT

A drip chamber for a medical fluid delivery system includes a housing having an inlet port and an outlet port, and defining a chamber between the inlet and outlet ports, the housing configured to channel medical fluid in a flow path from the inlet port through the chamber and to the outlet port. The inlet port includes a tubular member that extends into the chamber and redirects the path of the medical fluid against a side wall of the housing to reduce the velocity of the medical fluid and minimize formation of air bubbles in the medical fluid.

21 Claims, 4 Drawing Sheets

DRIP CHAMBER FOR MEDICAL FLUID DELIVERY SYSTEM

BACKGROUND OF THE INVENTION

1. Field of Invention

This invention generally relates to a medical fluid delivery system. More particularly, this invention relates to a drip chamber that minimizes the formation of air bubbles in a medical fluid delivery system.

2. Description of Related Art

Medical fluid delivery systems are used by medical personnel to inject nutrients and/or medication into a patient's body. "Medical fluid delivery systems," as used herein, include, for example, any system for delivering an intravenous solution such as glucose, saline solution, medical dyes, and medication in fluid form, to a patient. Such systems are used during surgery or when a patient is otherwise unable to ingest nutrients or medication orally.

An intravenous fluid delivery system, for example, generally includes a bag or container of intravenous fluid that is connected through a series of conduits to a needle inserted into a vein in the patient. The bag or container is supported at a higher elevation than the patient so that intravenous fluid flows through the conduits by the force of gravity.

One or more valves are disposed within the system to control the intravenous fluid flow rate. In addition, a drip chamber is disposed in the conduit arrangement between the intravenous fluid bag and the needle to allow medical personnel to visually inspect the "drip" (i.e., flow rate) of intravenous fluid through the system. From the drip rate, the flow rate of the infused fluid can be calculated. The drip chamber also provides a pocket for the collection of air in the system.

In particular, the drip chamber is constructed of a clear material and has a top inlet port connected to the conduit(s) leading to the intravenous fluid bag and a bottom outlet port connected to the conduit(s) leading to the needle. The inlet and outlet ports enclose opposite ends of a generally-cylindrical column, and fluid drips from the inlet downwardly through the column where it collects at the bottom of the column and exists via the outlet.

When infusing fluids intravenously, particularly under pressurized conditions (such as priming the chamber), the infused fluid flows at a high velocity from the drip chamber inlet opening into a pool of fluid contained in the bottom of the drip chamber. As the high velocity fluid impinges the pool surface, the bubbles are entrapped in the fluid pool, thus causing an air-bubble mixture to form. This requires a time-consuming effort to purge the air bubbles from the conduits leading to the patient. If air bubbles are not purged, they may enter the patient and cause an embolism or other harmful effects.

One solution to the problem is proposed in applicant's co-pending application Ser. No. 08/701,874, which is incorporated herein by reference. A member is positioned at an intermediate point within the chamber of the housing and directly in line with the flow path of the intravenous fluid. Under pressurized conditions, the fluid impinges on the member at a high velocity. The member effectively reduces the velocity of the fluid, thereby minimizing bubbles in the intravenous fluid pool. The member is attached to the side wall of the housing, which may, in some instances, increase manufacturing time and costs.

SUMMARY OF THE INVENTION

Accordingly, the present invention is directed to a drip chamber that substantially obviates one or more of the problems due to limitations and disadvantages of the related art.

To achieve these and other advantages and in accordance with the purpose of the invention, as embodied and broadly described, the invention comprises a housing having an inlet port and an outlet port and defining a chamber between the inlet and outlet ports, whereby medical fluid flows from the inlet through the chamber and exits via the outlet. The inlet port includes a tubular member that extends into the chamber. The tubular member is configured so that the medical fluid flowing from the inlet and through the tubular member is redirected against side walls of the chamber in order to reduce the velocity of the medical fluid.

Additional features and advantages of the invention will be set forth in the description which follows, and in part will be apparent from the description, or may be learned by practice of the invention. The objectives and other advantages of the invention will be realized and attained by the apparatus particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention. In the drawings.

DETAILED DESCRIPTION OF PREFERRED EMBODIMENTS

Reference will now be made in detail to the present preferred embodiments of the invention, examples of which are illustrated in the accompanying drawings. The exemplary embodiments refer to the use of a drip chamber in an intravenous fluid delivery system, although other medical fluid delivery systems are contemplated.

Figure 1:
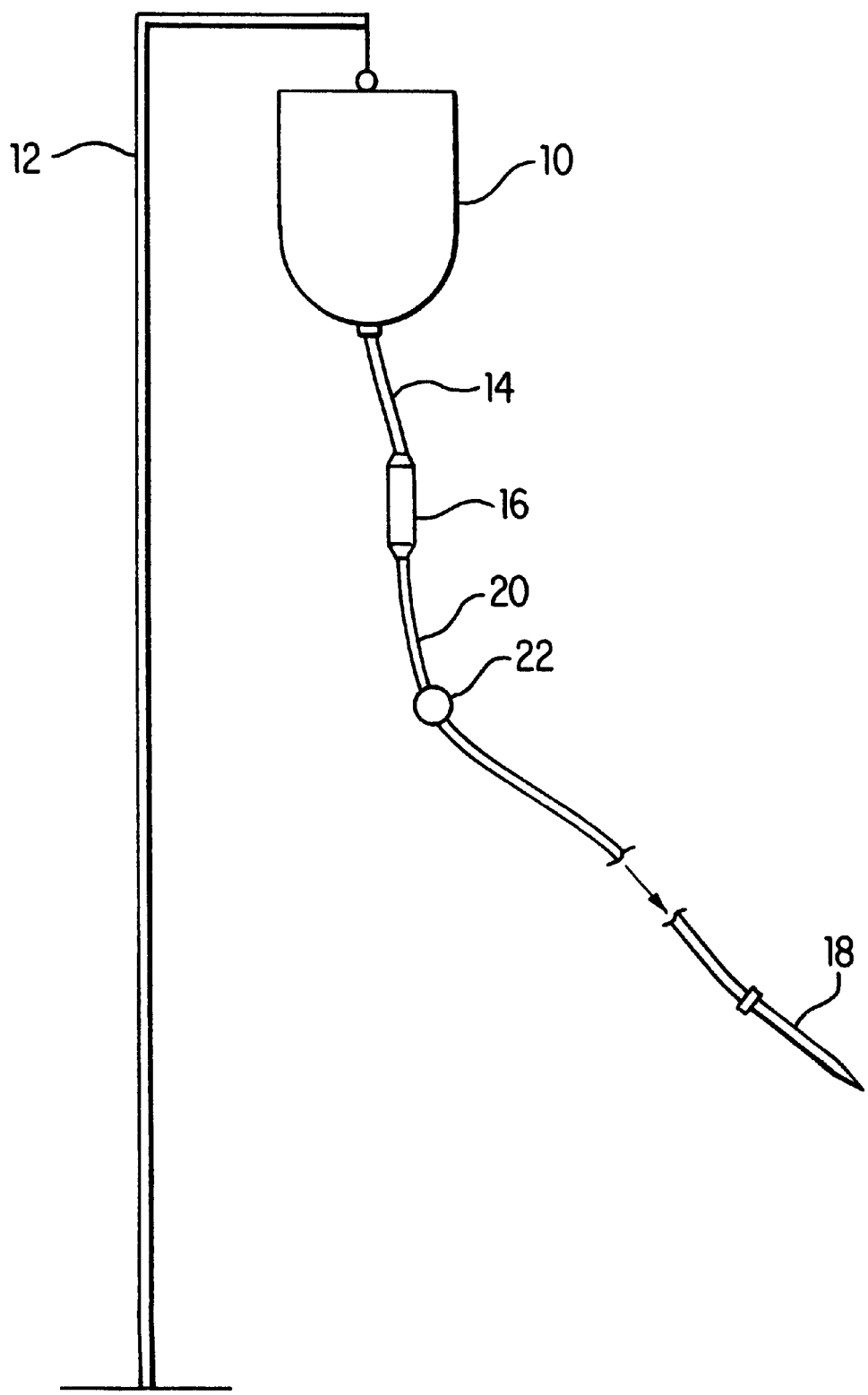
FIG. 1 is a diagram of a medical fluid delivery system including a drip chamber of the present invention.

An intravenous fluid delivery system in which the drip chamber of the present invention is used is shown in FIG. 1. The system generally includes an intravenous fluid bag or container 10 supported by a stand 12 at an elevation higher than the patient to effect intravenous infusion by gravitational force. The outlet of container 10 is connected through a conduit 14 to the inlet of a drip chamber 16. The outlet of the drip chamber 16 is connected to a needle 18 through a conduit 20. A valve 22 is located in the conduit 20 between the drip chamber outlet and the needle 18 to control the flow rate of the intravenous fluid. The needle 18 is then inserted into the vein of the patient to complete delivery of the fluid.

Figure 2:
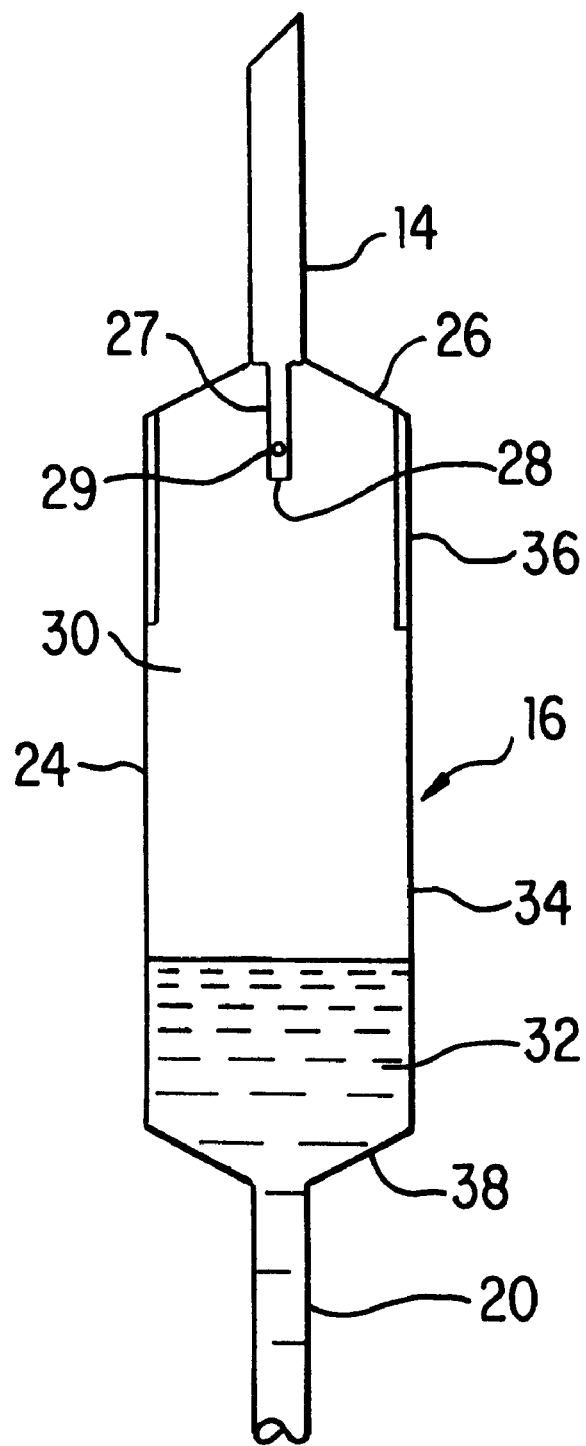
FIG. 2 is a front elevation view of a drip chamber of the present invention.

The drip chamber of the present invention is shown in greater detail in FIG. 2. The drip chamber 16 includes a substantially cylindrical housing 24 enclosed at its top end by an inlet port 26 and at its bottom end by an outlet port 38. The inlet port 26 is connected via conduit 14 in flow communication with the intravenous fluid bag 10. Outlet port 38 is connected via conduit 20 in flow communication with needle 18. The housing also defines an internal chamber or column 30 through which intravenous fluid flows, normally in droplet form.

Under normal operating conditions, intravenous fluid from bag 10 enters the drip chamber 16 through inlet port 26 and droplets fall from inlet port 26 through chamber 30 in a low-velocity "drip mode", where they collect in a pool 32 at the bottom of housing and eventually exit via outlet port 38. The rate at which the droplets fall through the chamber represents the flow rate of the system, which is controlled by valve 22. Since the system generally contains no mechanism for tracking the flow rate, the housing is preferably composed of a clear material to allow visual inspection of the "drip" or flow rate of the intravenous fluid through the system. Clear plastic or other suitable materials may be used for the housing.

One of the functions of the drip chamber is to prime the system at the beginning of a procedure or whenever a new bag 10 is added to the system. Priming is necessary to fill the conduits with intravenous solution and purge air from the system. To prime the system, drip chamber 16 is squeezed manually with valve 22 in the closed position. Release of the drip chamber creates negative pressure in the system and draws intravenous fluid from the bag and through the system. The valve is then opened, whereby a jet of intravenous fluid enters the chamber in this high velocity or "priming mode."

To allow compression of the drip chamber for priming, the housing of the embodiment in FIG. 2 is made of flexible, elastic material. Alternatively, housing 24 may include a flexible, lower portion 34 and a rigid upper portion 36 that will not flex when lower portion 34 is compressed.

The high-velocity jet of intravenous fluid entering drip chamber 16 during priming tends to form air bubbles in intravenous fluid pool 32 in the bottom of housing 24. To reduce entrapment of air bubbles in the pool, inlet port 26 of drip chamber 16 includes a tubular member 27 that extends longitudinally into chamber 30.

As shown in FIGS. 2–5, tubular member 27 is in fluid communication with conduit 14. Tubular member 27 has a closed end portion 28 that is crimped, capped, or otherwise closed to fluid flow. Tubular member 27 has one or more holes 29 formed about its periphery. A preferred embodiment of the present invention includes two holes formed 180° apart. However, it is envisioned that any desired number of holes can be formed in the periphery of tubular member 27, so long as the structural integrity of tubular member 27 is maintained. Tubular member 27 may be made of any suitable rigid or flexible material, such as stainless steel.

As a result of tubular member 27 having a closed end portion 28 and peripheral holes 29, the path of the intravenous fluid flow is redirected during priming of the system. Tubular member 27 is preferably configured so that during pressurized conditions the intravenous fluid flow will be re-directed against the side walls of housing 24 at a point above the level of intravenous fluid pool 32. During non-pressurized conditions, the intravenous fluid drips unimpeded into intravenous fluid pool 32 in droplet form so that the drip rate may be monitored by medical personnel.

Figure 3:
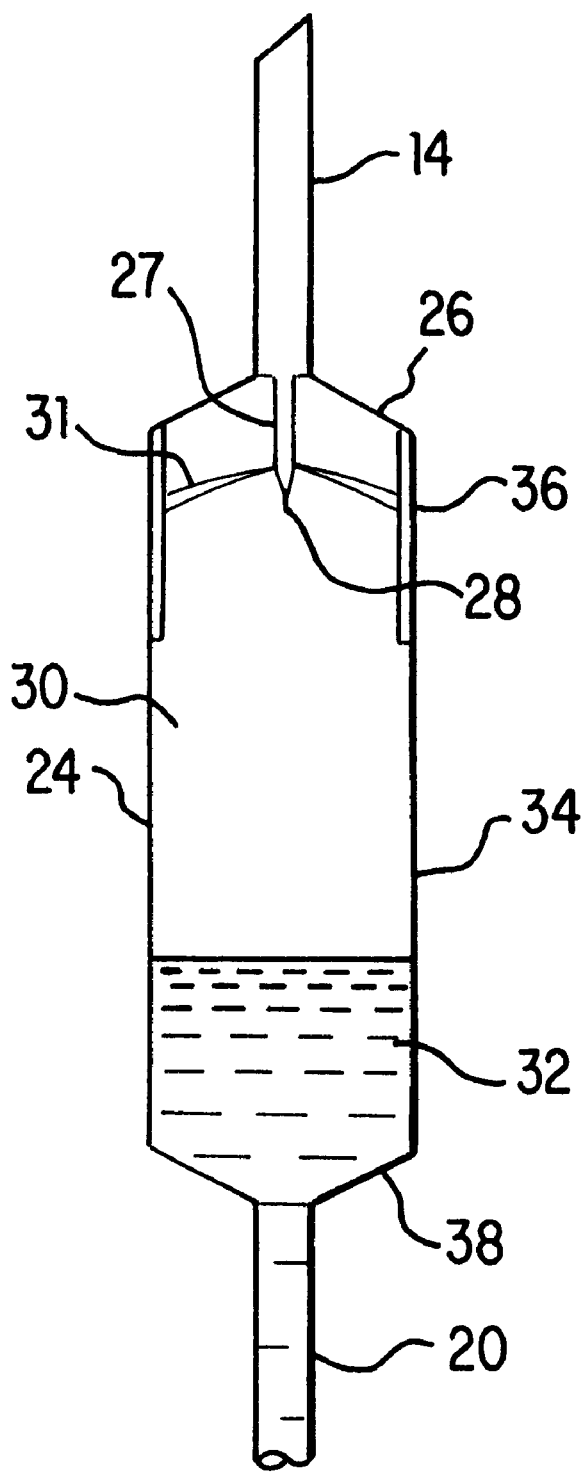
FIG. 3 is a side elevation view of the drip chamber shown in FIG. 2.
Figure 4:
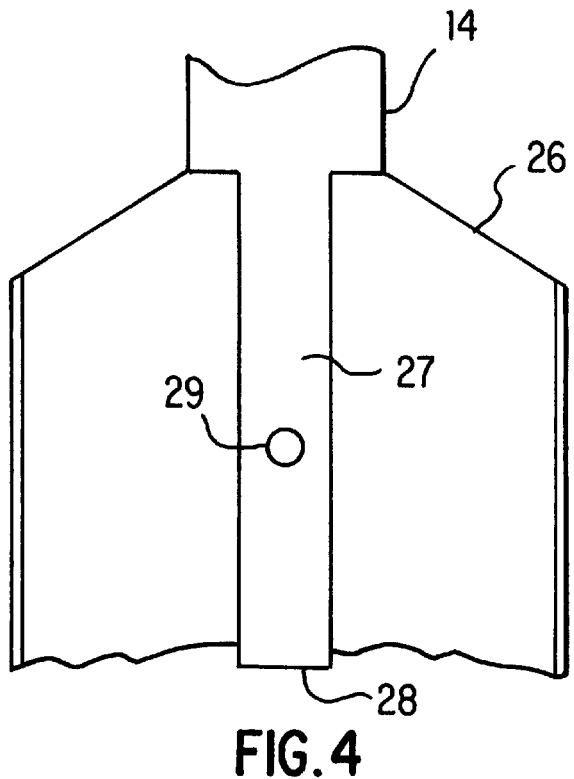
FIG. 4 is a front elevation view of an inlet port for the drip chamber of the present invention.
Figure 5:
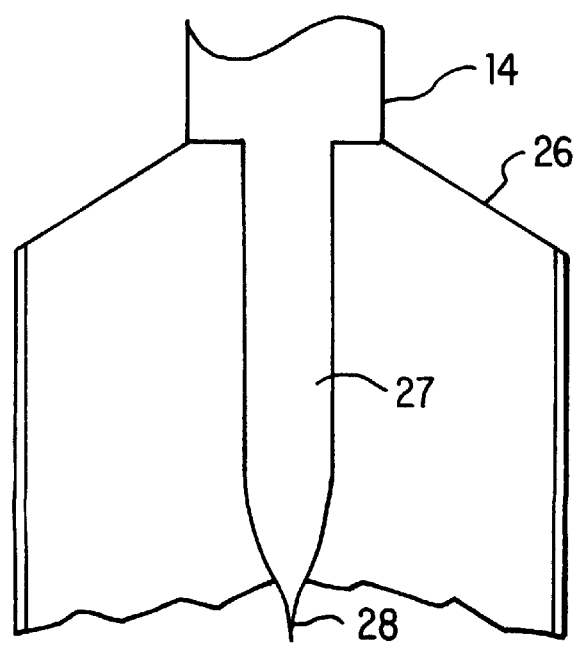
FIG. 5 is a side elevation view of the inlet port shown in FIG. 4.

FIG. 3 shows the drip chamber during a priming operation. A stream 31 of fluid exits through each hole 29 and impinges against the side walls of housing 24. The flow velocity (and kinetic energy) of the fluid is thereby decreased prior to its impingement on the surface of pool 32 in the drip chamber. The fluid then runs down the side walls of housing 24 and enters pool 32 at a lower velocity. Lowering the velocity of the fluid minimizes the formation of air bubbles in the pool. When the system is not being primed, fluid droplets of about 1/60 cc drip through the chamber.

Tubular member 27 and its peripheral holes 29 can exist in many configurations so long as they re-direct the fluid flow against the side walls of housing 24 at a point above the level of intravenous fluid pool 32. Therefore, holes 29 can be configured in various geometries, such as circles, ovals, squares, etc. Additionally, in a substantially circular configuration, the hole diameter is preferably selected to form droplets of about 1/60 cc. A hole diameter of about 0.015 inches may be used. The holes may be formed in member 27 by a laser, by a punch, by a molding process, or by any well known method in the art.

Tubular member 27 can also be configured in various geometries, such as circular, oval, and square cylinders. The cross-section of the tubular member may also vary at different points along its length.

It will be apparent to those skilled in the art that various modifications and variations can be made in the drip chamber of the present invention without departing from the spirit or scope of the invention. Thus, it is intended that the present invention cover the modifications and variations of this invention provided they come within the scope of the appended claims and their equivalents.

What is claimed is:

1. A drip chamber for a medical fluid delivery system, whereby fluid enters the drip chamber in one of a high velocity mode and a lower velocity, drip mode, the drip chamber comprising:

a housing having a side wall, an inlet port, and an outlet port, and defining a chamber between the inlet and outlet ports; and a tubular member extending into the chamber from the inlet port and having a first end in flow communication with the inlet port and a second, closed end opposite the first end, the tubular member positioned so that fluid flowing into the inlet port flows through the tubular member, the tubular member comprising a peripheral wall with at least one hole therethrough proximate the second, closed end, the second, closed end re-directing the fluid through the at least one hole so that, in the high velocity mode, and the fluid impinges against the side wall to minimize formation of air bubbles in the fluid collected in the chamber, the second, closed end re-directing the fluid in the drip mode flowing from the tubular member to a pool of fluid in the chamber without contacting the side wall, wherein the housing is substantially cylindrical with a constant diameter along its entire length, at least a portion of the length of the cylindrical housing is flexible.

2. The drip chamber of claim 1, wherein the tubular member is substantially concentric with the housing along its entire length.

3. The drip chamber of claim 1, wherein the housing has a substantially constant cross-section along its entire length.

4. The drip chamber of claim 1, wherein the tubular member comprises two holes positioned approximately 180° apart about the peripheral wall of the tubular member.

5. The drip chamber of claim 1, wherein the housing includes first and second portions, the second portion being substantially flexible to permit compression of the housing.

6. The drip chamber of claim 5, wherein the first portion is substantially rigid.

7. The drip chamber of claim 1, wherein the housing is substantially flexible the entire length to permit compression of the housing.

8. The drip chamber of claim 1, wherein the tubular member is substantially rigid.

9. The drip chamber of claim 1, wherein the tubular member is substantially flexible.

10. A drip chamber for a medical fluid delivery system, whereby fluid enters the drip chamber in one of a high velocity mode and a lower velocity, drip mode, the drip chamber comprising:

a housing having at least one wall defining a chamber for containing fluid, the housing having a longitudinal axis and an inlet and an outlet spaced from each other in a direction parallel to the longitudinal axis;

a tubular member in the chamber and defining a passageway in flow communication with the inlet, the passageway substantially parallel to the longitudinal axis along its length, the tubular member having at least one opening therein that is in the chamber, the at least one opening is substantially perpendicular to the longitudinal axis, the tubular member configured so that fluid flow from the tubular member and through the chamber in the drip mode is substantially parallel to the longitudinal axis, without contacting the at least wall, and that fluid flow in the high velocity mode is directed against the at least one wall of the housing, wherein the housing has a substantially constant cross-section along the longitudinal axis.

11. A medical fluid delivery system, comprising:

a medical fluid container;

a drip chamber including a housing having a side wall, an inlet port, and an outlet port, and defining a chamber between the inlet and outlet ports, and a tubular member extending into the chamber from the inlet port and having a first end in flow communication with the inlet port and a second, closed end opposite the first end, the tubular member positioned so that fluid flowing into the inlet port flows through the tubular member, the tubular member comprising a peripheral wall with at least one hole therethrough proximate the second, closed end, the second, closed end re-directing the fluid through the at least one hole so that, in a high velocity mode, the fluid impinges against the side wall to minimize formation of air bubbles in the fluid collected in the chamber, the fluid in a drip mode flowing from the tubular member to a pool of fluid in the chamber without contacting the side wall; and means, in flow communication with the outlet port of the drip chamber, for delivering the medical fluid to a patient.

12. The system of claim 11, wherein the housing is substantially cylindrical with a constant diameter along its entire length.

13. The system of claim 11, wherein the tubular member is substantially concentric with the housing along its entire length.

14. The system of claim 11, wherein the housing has a substantially constant cross-section along its entire length.

15. The system of claim 11, wherein the tubular member comprises two holes positioned approximately 180° apart about the peripheral wall of the tubular member.

16. The system of claim 11, wherein the housing includes upper and lower portions, the lower portion being substantially flexible to permit compression of the housing walls.

17. The system of claim 16, wherein the upper portion is substantially rigid.

18. The system of claim 11, wherein the housing is substantially flexible to permit compression of the housing.

19. The system of claim 11, wherein the tubular member is substantially rigid.

20. The system of claim 11, wherein the tubular member is substantially flexible.

21. A method for delivering medical fluid to a patient, comprising:

providing a medical fluid container in flow communication with the patient, with a drip chamber downstream of the fluid container and upstream of the patient, the drip chamber having a housing with an inlet port at one end of the housing and in flow communication with the medical fluid container and an outlet port at an opposite end of the housing, the housing defining a chamber between the inlet and outlet ports, the drip chamber further comprising a tubular member extending from the inlet port into the chamber and having a peripheral wall with at least one hole therethrough and a closed end proximate to the at least one hole;

compressing the drip chamber to facilitate a high velocity fluid flow from the fluid container into the drip chamber, whereby the tubular member directs the medical fluid against a side wall of the housing; and providing fluid flow in a lower velocity, drip mode, whereby fluid drips from the tubular member into a pool of fluid in the chamber without first contacting the side wall of the housing.

* * * * *